US006387408B1

(12) United States Patent
Illum et al.

(10) Patent No.: US 6,387,408 B1
(45) Date of Patent: May 14, 2002

(54) ADHESIVE DRUG DELIVERY COMPOSITION

(75) Inventors: Lisbeth Illum; Paul Williams; Antony James Caston, all of Nottingham (GB)

(73) Assignee: West Pharmaceutical Services Drug Delivery and Clinical Research Limited, Nottingham (GB)

(*) Notice: Subject to any disclaimer, the term of this patent is extended or adjusted under 35 U.S.C. 154(b) by 0 days.

(21) Appl. No.: 09/059,646

(22) Filed: Apr. 13, 1998

Related U.S. Application Data

(62) Division of application No. 08/234,723, filed on Apr. 28, 1994, which is a continuation of application No. 07/956,551, filed on Oct. 2, 1992, now abandoned, which is a continuation of application No. 07/689,926, filed as application No. PCT/GB89/01317 on Nov. 3, 1989.

(30) Foreign Application Priority Data

Nov. 8, 1988 (GB) ............................................. 8826116

(51) Int. Cl.[7] .......................... A61K 9/14; A61K 9/127; A61K 9/16; A61K 9/50; A61F 2/00
(52) U.S. Cl. ........................ 424/489; 424/450; 424/490; 424/491; 424/499; 424/426; 424/496; 424/497
(58) Field of Search .................................. 424/489, 464, 424/465, 881, 150.1, 139.1, 184.1, 185.1, 197.11, 234.1, 450, 490, 492, 496, 499, 426, 497, 491; 530/327

(56) References Cited

U.S. PATENT DOCUMENTS

| 4,443,549 A | * | 4/1984 | Sadowski ................. 424/150.1 |
| 4,615,697 A | | 10/1986 | Robinson |
| 4,661,345 A | * | 4/1987 | Tuomanen ............... 424/137.1 |
| 4,904,479 A | | 2/1990 | Illum |
| 5,204,108 A | | 4/1993 | Illum |
| 5,223,604 A | * | 6/1993 | Hodges et al. .............. 530/327 |
| 5,242,808 A | * | 9/1993 | Maugh et al. |
| 5,684,145 A | * | 11/1997 | Van Der Zee et al. |

FOREIGN PATENT DOCUMENTS

| GB | 2041517 A | | 9/1980 |
| WO | WO 85/02092 | | 5/1985 |
| WO | 85/02092 | * | 5/1985 |
| WO | WO 88/07078 | | 9/1988 |
| WO | WO-90/04963 A1 | * | 5/1990 |

OTHER PUBLICATIONS

Clark et al., Lectin–mediated mucosal delivery of drugs and microparticles, Advanced Drug Delivery Reviews, vol. 43, pp. 207–223 (Elsevier Science B.V. 2000).*

Harris, et al., "The Assessment of Muco–Adhesive Agents for Delaying Gastrointestinal Transit in Human Volunteers Using Gamma Scintigraphy," *Proceed. Int'l Symp. Control. Rel. Bioact. Mater.*. 14:12–13 (1987).

Park, et al., "Alternative Approaches to Oral Controlled Drug Delivery: Bioadhesives and in–Situ Systems" in *Recent Advances in Drug Delivery Systems* (Anderson & Kim, eds.) p. 163 (1984).

Park & Robinson, "Physico–Chemical Properties of Water Insoluble Polymers Important to Mucin/Epithelial Adhesion," *J. Controlled Release*, 2:47–57.

Robinson, et al., "Bioadhesive Polymers for Controlled Drug Delivery" in *Biological Approaches to the Controlled Delivery of Drugs* (Juliano, ed.) p. 307 (1987).

Harris, et al., *J. Controlled Release*, 12:45–53 (1990).

Illum, et al., *Methods in Enzymology*, 112:67–84 (1985).

Ofek, et al., "Adherence of *Escherichia coli* to human mucosal cells mediated by mannose receptors,"*Nature*, 265(5595):623–25 (1977).

Rao, et al.,"Studies on Factors Affecting the Biodhesion of coated Microparticles," *Proceed. Int'l Symp. Contol. Rel. Bioact. Mate*: 15: 103–04 (1988).

Khosla & Davis, *J. Pharm Pharmacol.*, 39:47–49 (1978).

Langer, et al., *J. Pharmaceutical Sciences*, 74(4):406–10 (1985).

Veillard, "IX. Buccal and Gastrointestinal drug Delivery System" in*Bioadhesion–Possibilities and future Trends*-(Gurney & Junginger, ed.) pp. 124–38 (1990).

* cited by examiner

Primary Examiner—Thurman K. Page
Assistant Examiner—Humera N. Sheikh
(74) Attorney, Agent, or Firm—Akin, Gump, Strauss, Hauer & Feld, L.L.P.

(57) ABSTRACT

Adhesive material from the fimbriae (esp. Type 1) of bacteria or synthetic analogues or fragments thereof is combined with a drug to provide for attachment to the gut of a mammal, thereby prolonging the transit time of the drug through the gut.

The 28 kDa polypeptide from *E. coli* Type 1 fimbriae is the preferred adhesive material ("adhesin"). The drug is presented in a carrier such as albumin, a polylactide/glycolide copolymer or alginate microcapsules. The adhesin may be incorporated in the carrier during preparation thereof, adsorbed onto the carrier after preparation, or covalently linked thereto, for example with carbodiimide.

26 Claims, No Drawings

SEQUENCE LISTING

<160> NUMBER OF SEQ ID NOS: 1

<210> SEQ ID NO 1
<211> LENGTH: 14
<212> TYPE: PRT
<213> ORGANISM: Escherichia coli -continued

```
<400> SEQUENCE: 1

Val Asp Ala Gly Thr Val Asp Gln Thr Val Gln Leu Gly Cys
1               5                   10
```

ADHESIVE DRUG DELIVERY COMPOSITION

CROSS-REFERENCE TO RELATED APPLICATIONS

This is a division of U.S. application Ser. No. 08/234,723, filed on Apr. 28, 1994, which is a continuation of U.S. application Ser. No. 07/956,551, filed on Oct. 2, 1992, abandoned, which is a continuation of U.S. application Ser. No. 07/689,926, filed on Jul. 8, 1991, abandoned, which corresponds to 371 PCT/GB89/01317, filed on Nov. 3, 1989, and GB 8826116.9, filed on Nov. 8, 1988.

The present invention relates to a drug delivery composition and more particularly to a drug delivery composition for administration via the gastrointestinal tract.

The gastrointestinal (G.I.) tract is one of the major routes for the administration of pharmacological agents. Drugs are normally well absorbed from the intestines, and dosage forms such as capsules, tablets and suspensions are well accepted by the general population. In recent years there has been a tendency towards the development of controlled release dosage forms that will provide therapy over an extended period of time. Normally this would be once a day and it is believed that such a change in dosage regimen will reduce adverse reactions and side effects and also improve patient compliance.

The design and evaluation of controlled release dosage forms must, however, take into account the properties of the gastrointestinal tract, including the rapid transit of material through the small intestine, which is the important site for absorption for certain drugs. Recent work by Davis and others at Nottingham University has shown that this transit time can be of the order of 3 hours or less. Thus the disadvantage of very long release times, for example 24 hours, is that the drug could have passed through the small intestine before being released and therefore its curative property could be effectively nullified.

A considerable advantage can be gained if the dosage form is held in the small intestine so that it will be well absorbed into the systemic circulation over a long period of time.

Recently, work has been done into investigating the use of synthetic polymers that may have muco- or bio-adhesive properties, for example those disclosed in WO 85/02092, such as cross-linked acrylic acid and methacrylic acid polymers. The problem with the use of synthetic polymers lies in the mode of action of such materials and in particular whether it is intended to attach dosage forms to the mucus, which should easily slough off, or to attach dosage forms to the glycocalyx or directly to the cell surface of the enterocyte. Various in vitro tests conducted with excised portions of stomach and oesophagus are not considered to be realistic in terms of in vivo environmental conditions and transit phenomena.

It is an object of preferred aspects of the present invention to provide a drug delivery system for use in the gastrointestinal tract which obviates the above disadvantages and maintains the drug in the G.I. tract, for example in the small intestine, for a prolonged period thereby allowing the drug to be released at a desired rate over this prolonged period. By extending the period, the drug can if required be released more slowly, which may lead to less severe adverse reactions and side effects.

The present invention therefore provides a drug delivery system, preferably including a plurality of particles containing active drug material, preferably size 20 microns or less, and incorporating on the outer surface of at least some of the particles a bioadhesive material derived from a bacterium such that in use the bioadhesive material will adhere to the small intestine of the gut.

The term "drug" is used herein to include any pharmacologically active compound or antigen-comprising material.

The term "bioadhesive" is used to denote a material which adheres to the gut wall. The bioadhesive derived from a bacterium may be isolated therefrom or may be a synthetically prepared version thereof, or an analogue or fragment of such material.

Such bioadhesive materials have been previously proposed for use in medicine in WO 88/07078, but only as immobilising materials for binding biological material to a carrier, for example binding a blood clotting agent to a carrier substance. There was no suggestion that the bioadhesives could be used to direct medicaments to the gut wall.

The micro-organisms from which the adhesive material is derived or to which it corresponds will generally be those found in the G.I. tract, especially the (small) intestine, of the mammal being treated. Such micro-organisms include *E. coli*, Klebsiella spp. and Salmonella spp.

Preferably, the bioadhesive material is obtained from *Escherichia coli*, especially a human G.I. tract infesting strain thereof, or corresponds to such material.

In the small intestine certain bacterial flora are found to adhere extremely well. *Escherichia coli*, for example, adheres via surface proteins called fimbriae (pili). *E. coli* strains express the following fimbrial types:

(a) Type 1 or 'common' fimbriae whose adhesive properties are inhibited by mannose (mannose-sensitive fimbriae).

(b) P fimbriae (mannose-resistant).

(c) Colonisation factor antigens (CFAI and CFAII) which are mannose-resistant.

The present invention is concerned particularly with class (a). These materials, when purified, can be identified by the ability to haemagglutinate guinea-pig erythrocytes in the absence but not in the presence of α-methylmannoside. In the case of Type 1 fimbriae from *E. coli*, the presence of a 17 kDa sub-unit protein may be detected on sodium dodecyl sulphate polyacrylamide gel electrophoresis after denaturation of fimbriae by saturated guanidine HCl. In other organisms, such as Klebsiella spp. the corresponding sub-unit may be slightly larger or smaller. Finally, Type 1 fimbriae material from a given organism would be expected to react in Dot and Western Immunoblots with a polyclonal antiserum raised against the Type 1 fimbriae from the same organism. The various test methods for all three of these tests are standard.

Type 1 fimbrial material from *E. coli* has previously been isolated and shown to comprise polypeptides of molecular weights of about 14 kDa, 17 kDa and 28 kDa. See, for example, Hanson & Brinton, Nature 332, 265 (1988) and Hanson et al, *J. Bact.* 170(8), 3350 (1988). The 28 kDa polypeptide described therein is probably the same as the 29 kDa FimH polypeptide described by Abraham et al, (1988) *Infect. & Immun.* 56(5), 1023–1029. This latter paper suggests using FimH in a vaccine to confer immunity against *E. coli* binding, but does not suggest using FimH to bind a drug or antigen to the gut wall. The 17 kDa polypeptide is the major polypeptide. Since micro-organisms can adhere firmly in the gastrointestinal tract through this adhesion process (which may be through an interaction between the adhesive molecule ("adhesin") and sugar residues, eg mannosides, in the gastrointestinal tract) it is possible in accordance with the present invention to achieve similar adhesive effects by the isolation and purification of an individual adhesin polypeptide. When administered to rabbits the adhesin is seen to adhere to the gastrointestinal tract.

Alternatively, the larger bodies known as "fimbriosomes" may be used. These bodies are described in Abraham et al, *Infect. & Immun.* 56(5), 1023,(1988).

In the present invention adhesins and similar bioadhesive materials produced from micro-organisms are used to design and develop controlled release dosage forms with extended gastrointestinal residence. The delivery system preferably consists of small particles (a few microns in size) so that the adhesive is able to attach the particle to the wall of the gastrointestinal tract through sugar residue, lectin-mediated processes. The adhesins may be coated onto particles or covalently bound (grafted) onto the surface of the particle. A preferred adhesin is the bacterial adhesin obtained from *E. coli*, but there are many other adhesin-producing bacteria available, for example *Pseudomonas aeruginosa*.

It is also apparent that the adhesive characteristics of the fimbrial material do not necessarily reside in the complete fimbrial structure and that a suitably cleaved product or its synthetic equivalent comprising the correct sequence of amino acids demonstrates similar bioadhesive properties. The preparation of a peptide of this sort is described in Abraham & Beachey, *J. Bact.* 169(6), 2460, (1987). More specifically, the peptide consisted of residues 23–35 of *E. coli* Type 1 fimbrial protein namely VDAGTVDQTVQLGC (i.e. Val-Asp-Ala-Gly-Thr-Val-Asp-Gln-Thr-Val-Gln-Lys-Gly-Cys) (SEQ ID. NO:1). Such a peptide may be made by conventional techniques.

Likewise, synthetic polymers with a similar structure to that of the adhesin will generally have the same effect in enhancing the interaction between the wall of the small intestine and administered colloidal particles. Purified adhesin materials or synthetic analogues may be used as macromolecular carriers where the drug is attached to the adhesin molecule directly and not necessarily within a microparticle.

The attachment of fimbriae to the surface of drug-containing particles may be by adsorption (hydrophobic region of peptide to hydrophobic surface of a suitable particle, for example polymeric microsphere, polystyrene, polymethylmethacrylate, polyalkylcyanoacrylate, emulsion (triglyceride)), or by covalent attachment. Mechanisms for linking proteins to microspheres are given in Illum & Jones, Methods in Enzymology 112, 67–84 (1985).

Other ways of attaching the protein include modification of a particle surface by adsorption or covalent attachment of suitable linking groups to which the protein may be subsequently attached. Examples here include albumin, gelatin, dextran, alginate, polylactide/glycolide, polyhydroxybutyrate, polyanhydride microspheres and liposomes.

Dry formulations are to be preferred but suspensions in a suitable vehicle (for example, polyethylene glycol or triglyceride oil) may also be used. An actual drug formulation preferably involves the preparation of a multiparticulate drug containing system (size preferably below 1 mm) such as a microsphere or microcapsule. Drug entrapment may be performed during preparation (e.g. emulsification, polymerisation) or after (remote loading).

The fimbrial material may be included in the particle preparation step (if it can be attached to the particle surface; proteins are good stabilizers of emulsions) or grafted onto the surface during a polymerization stage. Alternatively the material may be attached by adsorption or covalent linkage after the particles have been prepared.

The concept is readily applicable to many, if not all, drugs given orally, including cephalosporins, chlorthiazide, isosorbide and frusemide (which are absorbed in the (upper) regions of the small intestines) and peptides which are intended for absorption in the colon, for example insulin, growth hormone, calcitonin, interferon and tumour necrosis factor.

Preferred embodiments of the present invention will now be described by way of examples.

EXAMPLE 1

Type 1 fimbriae were obtained from *Escherichia coli* AD9777, by culturing in nutrient broth. Agglutination properties were checked using guinea pig red blood cells. The bacteria were collected by centrifugation and the fimbriae were removed by use of a microfluidizer apparatus (Microfluidics Corporation) in a manner described in more detail below. The crude preparation was centrifuged and freeze dried. The proteins were then characterized by SDS polyacrylamide gel electrophoresis. Antibodies to bacterial Type 1 fimbriae were raised in rabbits for subsequent use in analytical procedures (inmunoblotting, ELISA).

The fimbrial proteins are obtained as follows. In order to simplify the harvesting of the fimbrial proteins and to ensure consistency in the preparation, a microfluidizer (Model M110, Microfluidics, Newton, Mass., USA.) was used. This is a high pressure homogeniser used conventionally for the preparation of emulsions. It is based on the submerged jet theory in which two similar streams travelling at very high velocities interact in precisely defined microchannels. The interaction of the two streams, in this case bacterial suspensions, disrupts the cells. Having grown and isolated the bacteria, a 2% w/v suspension was made. This was then added to the microfluidizer and subjected to a series of increasing pressures: 500 psi to 6000 psi (3.4 to 41.4 $MNm^{-2}$). At each pressure the suspension was cycled through the apparatus four times, then spun in a cool centrifuge. The supernatant was collected and stored at 4° C. and the pellet was resuspended and the process repeated at a higher pressure. Once the bacterial suspension became translucent it was assumed that the cells had been totally disrupted, hence no further increase in pressure was necessary. The supernatants were freeze-dried, and the proteins present were studied by SDS polyacrylamide gel electrophoresis (SDS-PAGE). The gel showed that at a pressure of 500 psi (3.4 $MNm^{-2}$) the majority of the fimbrial proteins were stripped off with little contaminating proteins present; at 6000 psi (41.4 $MNm^{-2}$) the bacteria had been totally disrupted.

It is found that the purified fimbrial material can cause agglutination of red blood cells on its own or when attached to a model colloidal particle, polystyrene latex. This agglutination effect could be blocked using mannose, indicating that the agglutination was, as expected, mediated by binding to a mannose-specific site (lectin-mediated).

EXAMPLE 2

In Vitro Binding

The ability of Type 1 fimbrial proteins to adhere to the small intestine was measured in an in vitro preparation of gut-sacs from the rat small intestine. A length of evacuated rat small intestine was tied at one end using a ligature, and then 1 ml of a fimbrial suspension (100 ng/ml) carefully added. The fimbrial suspension was prepared from fimbriae obtained as above and suspended in phosphate buffered saline at pH7.4. Having tied the other end of the intestine, again with a ligature, to form a sac, it was incubated in a flask containing 20 ml of oxygenated incubation medium at 37° C. After 30 minutes the sac was removed and the fimbrial suspension sampled. The fimbrial content was assayed by the Dot-blot method. Each experiment was performed in triplet, with and without α-methyl mannoside.

The results from the Dot-blots indicated that the fimbrial proteins were depleted from the medium and were adhering to the intestine.

EXAMPLE 3

In Vivo Binding of Adhesins

Type 1 fimbrial proteins, prepared as above, were labelled with iodine-125, by the normal method for labelling proteins, the Iodogen method, to allow detection of the proteins in biological tissues easier.

A suspension of the iodide-125 labelled proteins was administered to the isolated small intestine of an anaesthetised fasted rat (300 g adult Wistar). The animal was maintained in an anaesthetised state for two hours after which it was killed. The entire small intestine was removed and sectioned into 1 cm. sections which were assessed for radioactivity using a gamma counter. An activity profile for each animal was plotted to show the distribution of the activity and the total amount of activity associated with the intestine was calculated. Co-administration of various adherence inhibitors showed that the activity was associated with the fimbrial proteins and not free iodine-125 released from the I-125 labelled fimbrial proteins. A total of 15–20% more activity was associated with the intestine when fimbrial proteins were added in the absence of inhibitors compared with their administration in the presence of inhibitors. Inhibitors used included unlabelled fimbrial proteins and α methyl-mannoside.

EXAMPLE 4

In Vivo Binding of Coated Particles

Following the work outlined in Example 3, model particles were coated with Type 1 fimbriae and these coated particles were administered to the intestine as described. The polystyrene particles used were labelled with iodide-125 by irradiating them in a cobalt-60 source in the presence of iodide-125. The particles were cleaned and coated with fimbrial proteins. An aliquot of particles were mixed with a suspension of fimbrial proteins for a 24 hour period at room temperature. After this time the particles were centrifuged and the supernatant discarded. The fimbrial coated particles (otherwise known as sensitised) were administered to an animal as previously described. The same procedure for assessing the results was used for the sensitised particles as for free fimbriae. The activity profiles and the total activity recovered were plotted. A mean total percentage of activity retained in the small intestine for each experimental series was calculated and this value for each was plotted. Student's "T"-tests on these values have also been calculated.

The results show that the sensitised particles significantly adhere to the small intestine of the rat. Values of the average percentage of activity recovered in the intestine range from 35 to 40%, with experimental values 15 to 20% greater than the controls. Statistical analysis of this data shows it to be significant to 95% confidence limits.

FORMULATIONS

Albumin as carrier

The formulation is prepared by the following process. An aqueous albumin solution is added to the drug and the resulting aqueous solution is dispersed in oil (with a suitable surfactant) to provide a water-in-oil emulsion. The product is heated in order to denature and cross-link the albumin, thereby providing microspheres, which are then washed. Finally, fimbrial material is attached to the microspheres by adsorption or by covalent linkage (using carbodiimide or another bifunctional coupling agent).

Polylactide/glycolide as carrier. A polylactide/glycolide copolymer is first dissolved in a solvent which is also a solvent for the drug and an oil-in-water type of emulsion is prepared using the resulting solution. Solvent is removed from the emulsion to leave solid microspheres containing the drug. Finally, fimbrial material is attached by adsorption or by covalent linkages as above. Alternatively, the microspheres may be prepared using a double emulsion (water-in-oil) process.

Alginate Microcapsules. The drug is first dissolved in a sodium alginate solution and drops of alginate are added to calcium chloride solution to form microcapsules. These are then separated and the fimbrial material is attached to the surface of the microcapsules as above.

In all examples, the fimbrial material can alternatively be included in the emulsification stage, which may be advantageous, especially for the oil-water formulations. The entrapment of the pilus material in an emulsion or liposome may be achieved by linking the protein to a lipid (such as a fatty acid), to a phospholipid (such as phosphatidylethanolamine) or to a steroid (such as cholesterol). The fatty portion should then fit well into the emulsion/liposome in an analogous manner to monoclonal antibodies, as is known in the art .(see., for example, Illum & Jones, op. cit.).

If desired, the formulations of the invention may be coated with an enteric coating which will protect the drug and the adhesins from acidic or proteolytic digestion in the stomach and then dissolve, leaving the adhesins exposed for binding to the intestinal wall.

What is claimed is:

1. A drug delivery composition comprising
   particles comprising a drug and a bacterial bioadhesive material binding via a sugar residue, lectin-mediated process to the small intestine of a mammal,
   wherein the bioadhesive material is incorporated on the surface of the particles either by coating or covalent binding.

2. A composition according to claim 1 wherein the drug is present as a plurality of particles.

3. A composition according to claim 2 wherein the particles have an average diameter of 20 microns or less.

4. A composition according to claim 2 or 3 wherein the bacterial bioadhesive material is covalently attached to the drug particles.

5. A drug delivery composition for sustained release of a drug in the gastrointestinal tract comprising:
   liposomes or an emulsion having incorporated therein;
   at least one drug, and
   a bacterial bioadhesive material binding to the small intestine of a mammal via a sugar residue, lectin-mediated process, wherein the bioadhesive material is linked to a lipid entrapped in the liposomes or emulsion, and wherein the liposomes or emulsion are bound to the small intestine by the bioadhesive material to permit sustained release of the drug to the gastrointestinal tract of a mammal.

6. A composition according to claim 1 or 5 wherein the bacterial bioadhesive material is found in the Type 1 adhesin of E. coli.

7. A composition according to claim 6 wherein the bacterial bioadhesive material comprises a 28 kDa polypeptide of E. coli adhesins.

8. A process for preparing a composition according to claim 1 or 5 comprising combining a drug, a carrier incorporating the drug and a bacterial bioadhesive material binding to the small intestine of a mammal via a sugar residue, lectin-mediated process, wherein the bacterial bioadhesive material is incorporated on the surface of the carrier.

9. A method of treating a mammal comprising administering orally to the mammal a therapeutically effective amount of a drug delivery composition comprising polymeric particles, having incorporated therein a drug and having coupled to the surface a bacterial bioadhesive material binding to the small intestine of a mammal via a sugar residue, lectin-mediated process for a period of time permitting controlled release of the drug to the gastrointestinal tract of the mammal.

10. The method of claim 9 wherein the bioadhesive material is covalently attached to the particles.

11. The method of claim 9 wherein the bioadhesive material is a surface adhesin polypeptide of a bacterium.

12. The method of claim 10 wherein the bioadhesive material is a fimbriae or portion thereof from E. coli.

13. The method of claim 9 wherein the particles consist of a polymeric drug.

14. The method of claim 9 wherein the drug is selected from the group consisting of cephalosporins, chlorthiazide, isosorbide and frusemide.

15. The method of claim 9 wherein the drug is selected from the group consisting of insulin, growth hormone, calcitonin, interferon and tumor necrosis factor.

16. The method of claim 9 wherein, after the particles are adhered to the small intestine, the drug is released from the particles and absorbed in the upper regions of the small intestine.

17. The method of claim 9 wherein, after the particles are adhered to the small intestine, the drug is released from the particles and absorbed in the colon.

18. The composition of claim 1 wherein the bioadhesive material is a surface adhesin polypeptide of a bacterium.

19. The composition of claim 1 wherein the bioadhesive material is a fimbria or portion thereof from E. coli.

20. The composition of claim 1 wherein the particles are formed of a polymer selected from the group consisting of polystyrene, polymethylmethacrylate, albumin, gelatin, dextran, alginate, polylactide, polyglycolide, copolymers of polylactide glycolide, polyhydroxybutyrate and polyanhydride microspheres.

21. A method of treating a mammal comprising administering orally to the mammal a therapeutically effective amount of a drug delivery composition comprising
   liposomes or an emulsion having incorporated therein at least one drug, and
   a bacterial bioadhesive material binding via a sugar residue lectin-mediated process to the small intestine, which is linked to a lipid entrapped in the liposomes or emulsion, and which adheres to the small intestine for a period of time permitting controlled release of the drug.

22. The method of claim 21 wherein the bacterial bioadhesive material is a fimbria or portion thereof from E. coli.

23. The composition according to claim 2 wherein the bacterial bioadhesive material is found in the Type 1 adhesin of E. coli.

24. The composition according to claim 3 wherein the bacterial bioadhesive material is found in the Type 1 adhesin of E. coli.

25. The composition according to claim 4 wherein the bacterial bioadhesive material is found in the Type 1 adhesin of E. coli.

26. The composition according to claim 5 wherein the bacterial bioadhesive material is found in the Type 1 adhesin of E. coli.

* * * * *